US006066640A

United States Patent [19]
Uckun et al.

[11] Patent Number: 6,066,640
[45] Date of Patent: May 23, 2000

[54] HYDROXY-HALO-QUINAZOLINES FOR AUGMENTATION OF MAST CELL BACTERICIDAL ACTIVITY

[75] Inventors: Fatih M. Uckun, White Bear Lake; Ravi Malaviya, Shoreview, both of Minn.

[73] Assignee: Hughes Institute, Roseville, Minn.

[21] Appl. No.: 09/264,141

[22] Filed: Mar. 5, 1999

[51] Int. Cl.$^7$ .................................................. A61K 31/517
[52] U.S. Cl. ........................................... 514/259; 514/267
[58] Field of Search ...................................... 514/259, 267

[56] References Cited

PUBLICATIONS

Barriere, S. L. et al. (Feb. 1995), *Critical Care Medicine*, 23(2):376–393 "An overview of mortality risk prediction in sepsis.".

Echtenacher, B. et al. (May 2, 1996), *Nature*, 381:75–77 "Critical protective role of mast cells in a model of acute septic peritonitis."

Goodman, P.A. et al. (Jul. 10, 1998), *The Journal of Biological Chemistry*, 273(28):17742–17748 "Role of Tyrosine Kinases in Induction of the c–jun Proto–oncogne in Irradiated B–lineage Lymphoid Cells."

Malaviya, R. et al. (1994), *Journal of Immunology*, 152(4):1907–1914 "Mast Cell Phagocytosis of FimH—Expressing Enterobacteria."

Malaviya, R. et al. (1995), *Methods in Enzymology*, 253:27–43 "Interaction of Bacteria with Mast Cells."

Malaviya, R. et al. (1996), *Journal of Immunology*, 156(4):1490–1496 "Mast Cells Process Bacterial Ags through a Phagocytic Route for Class I MHC Presentation to T Cells."

Malaviya, R. et al. (Apr. 1994), *J. Clin. Invest.*, 93:1645–1653 "Mast Cell Degranulation Induced by Type 1 Fimbriated *Escherichia coli* in Mice."

Malaviya, R. et al. (Mar. 5, 1993), *The Journal of Biological Chemistry*, 268(7):4939–4944 "Reversible Translocation of 5–Lipoxygenase in Mast Cells upon IgE/Antigen Stimulation."

Malaviya, R. et al. (May 2, 1996), *Nature*, 381:77–80 "Mast cell modulation of neutrophil influx and bacterial clearance at sites of infection through TNF—α."

Qureshi, R. et al. (Sep. 15, 1988), *The Journal of Immunology*, 141(6):2090–2096 "The Role of Mast Cells in Thioglycollate—Induced Inflammation."

Schifferli, D. M. et al. (Nov. 1988), *Antimicrobial Agents and Chemotherapy*, 32(11):1609–1613 "Bacterial Adhesion: Modulation by Antibiotics with Primary Taragets Other than Protein Synthesis."

Sher, A. (Sep. 23, 1976), *Nature*, 263:334–336 "Complement–dependent adherence of mast cells to schistosomula."

Sher, A. et al. (1979), *Laboratory Investigation*, 41(6):490–499 "Complement Receptors Promote the Phagocytosis of Bacteria by Rat Peritoneal Mast Cells."

Sher, A. et al.(Sep. 1983), *The Journal of Immunology*, 131(3):1460–1464 "Mechanisms of Protective Immunity Against *Schistosoma Mansoni* Infection in Mice Vaccinated with Irradiated Cercariae. IV. Analysis of the Role of IgE Antibodies and Mast Cells."

Tewari, R. et al. (Feb. 5, 1993), *The Journal of Biological Chemistry*, 268(4):3009–3015 "Neutrophil Activation by Nascent FimH Subunits of Type 1 Fimbriae Purified from the Periplasm of *Escherichia coli*."

van den Broek, P.J. (Mar.–Apr. 1989), *Reviews of Infectious Diseases*, 11(2):213–245 "Antimicrobial Drugs, Microorganisms, and Phagocytes."

Xu, L. et al. (1993), *Prostaglandins*, 45:385–398 "Effect of Culture Conditions on Mast Cell Eicosanoid Synsthesis."

*Primary Examiner*—Phyllis G. Spivack
*Attorney, Agent, or Firm*—Merchant & Gould P.C.

[57] ABSTRACT

Hydroxy-halo quinazolines for the augmentation of mast cell anti-microbial activity are disclosed.

15 Claims, 8 Drawing Sheets

HYDROXY-HALO-QUINAZOLINES FOR AUGMENTATION OF MAST CELL BACTERICIDAL ACTIVITY

FIELD OF THE INVENTION

The present invention relates generally to the potentiation and enhancement of mast cell antibacterial activity and bacterial clearance in a patient, particularly in patients having defects in the phagocytic components of the immune system by the administration of the hydroxy-halo-quinazoline derivatives.

BACKGROUND OF THE INVENTION

Sepsis is the major cause of morbidity and mortality in immunocompromised patients due to neutropenia following chemotherapy or radiotherapy. Recent advances in cancer management such as bone marrow transplantation, and the use of intensive chemotherapy and radiation therapy have added substantially to the number of patients that have survived cancer but due to the seriously impaired host defense system have lost their ability to resist or contain infections. Beside antibiotic therapy, an orchestrated response of the immune defense system towards bacteria is imperative in controlling and rapidly eliminating the offending pathogen.

Mast cells are functionally versatile and anatomically ubiquitous elements of the immune system capable of phagocytosing gram negative bacteria such as *Klebsiella pneumoniae* and *E. coli*. Recent studies using mast cell-deficient mice have provided unprecedented experimental evidence that mast cells play a pivotal role in host innate immune defense against gram negative bacterial infections by killing gram negative bacteria and recruiting neutrophils to the sites of active infection through the release of TNFα (Malaviya, R., et al., 1996, *Nature*, 381 (6577):77–80 and Echtenacher, et al., 1996, *Nature*, 381 (6577):75–7). Since mast cells are strategically located at the host environment interface, mast cells should be the first cell type to encounter invading pathogen. Augmenting bactericidal activity of mast cells would improve bacterial clearance and may rescue neutropenic patients from fatal consequences of gram negative bacterial infections.

Like effector cells of the innate immune system, mast cells are able to discern a variety of infectious agents that attach to them. It has been previously shown that mast cells could bind and phagocytose gram negative bacteria such as *E. coli, K. pneumoniae, E. cloaece*, and *S. typhimurium*. (Malaviya, R., et al., 1994, *J. Immunol.*, 152 (4):1907–14 and Sher, A., et al., 1979, *Lab Invest.*, 41(6):490–9). The mechanism of mast cell bactericidal activity involves generation of superoxide anion (Malaviya, R., et al., 1994, *J. Immunol.*, 152 (4):1907–14). The killing of *Shistosoma mansoni* by mast cells have been shown to be mediated by the mast cell granule associated enzymes chymase or rat mast cell protease II (Sher, A., 1976, *Nature*, 263 (5575): 334–6 and Sher, A., et al., 1983, *J. Immunol.*, 131(3): 1460–5).

In a systematic search to identify a potentiator of mast cell bactericidal activity, we identified 4-(3'bromo-4'-hydroxylphenyl)-amino-6,7-dimethoxyquinazoline, WHI-P154 as a lead compound. WHI-P154 increased phagocytosis and killing of *E. coli* in vitro and bacterial clearance in vivo. WHI-P154 and structurally similar active hydroxy-halo-quinazoline derivatives provide a novel approach to combat infections by augmenting bactericidal activity of mast cells, which has applications in clinical settings.

SUMMARY OF THE INVENTION

Novel halo-hydroxy quinazoline derivatives defined below in structural formula I, and particularly 4-(3'bromo-4'-hydroxylphenyl)-amino-6,7-dimethoxyquinazoline (WHI-P154) are demonstrated herein to potentiate the bactericidal activity of mast cells against *E. coli*. The potentiation by halo-hydroxy quinazoline was observed in assays which measured a reduction in colony forming units (CFU) on agar media. Enhanced bacterial clearance and prevention of bacterial-induced sepetic shock was also demonstrated in vivo on administration of the halo-hydroxy quinazolines.

The structure activity relationship of tested compounds suggests that the halo substitution on the phenyl ring likely contributes to the activity of WHI-P154, since WHI-P131 and WHI-P132, lacking the bromo substituent, were not active. Further, the single bromo substitution at the 3' position is responsible for the activity, since introduction of a second bromo group at the 5' position of the phenyl ring did not improve activity (WHI-P97).

This potentiation of mast cell bactericidal activity provides a novel approach to the treatment of bacterial infection. The hydroxy-halo compounds of the invention, and particularly WHI-P154, can be administered to patients to treat bacterial infections and prevent septic shock. This therapeutic method is particularly effective in patients with neutropenia, i.e., defects in neutrophil number or function. Administration of the hydroxy-halo compounds of the invention, and particularly WHI-P154, potentiates the antibacterial action of mast cells. In a preferred embodiment, the hydroxy-halo compound is conjugated to a targeting moiety, e.g., an antibody, which specifically targets the compound to mast cells.

BRIEF DESCRIPTION OF THE DRAWINGS

FIG. 1 is a graph showing the effect of 6,7-dimethoxyquinazolines on mast cell bactericidal activity. Mast cell monolayers were incubated with *E. coli* ORN103 (pSH2) in the presence and absence of test compounds. The percentage of bacterial viability was determined by comparing the viable bacteria associated with vehicle treated mast cell monolayers at 0 minutes and the viable bacteria associated with vehicle treated and drug treated monolayers at 30 minutes. The number of viable bacteria associated with vehicle treated/ monolayers of mast cells at 0 minutes were $3.69 \pm 0.22 \times 10^5$ CFU. The data points represent the mean± SEM of duplicates from 2–3 independent experiments.

The data points represent the mean ± SEM values from 3–4 independent experiments.

DETAILED DESCRIPTION OF THE INVENTION

Definitions

All scientific and technical terms used in this application have meanings commonly used in the art unless otherwise specified. As used in this application, the following words or phrases have the meanings specified.

Halo is fluoro, chloro, bromo, or iodo. Alkyl, alkanoyl, etc., denote both straight and branched groups; but reference to an individual radical such as "propyl" embraces only the straight chain radical, a branched chain isomer such as "isopropyl" being specifically referred to. $(C_1-C_4)$Alkyl includes methyl, ethyl, propyl, isopropyl, butyl, iso-butyl, and sec-butyl; $(C_1-C_4)$alkoxy includes methoxy, ethoxy, propoxy, isopropoxy, butoxy, iso-butoxy, and sec-butoxy; and $(C_1-C_4)$alkanoyl includes acetyl, propanoyl and butanoyl.

As used herein, "pharmaceutically acceptable carrier" means any material which, when combined with the compound of the invention, allows the compound to retain biological activity, such as the ability to potentiate antibacterial activity of mast cells and macrophages. Examples include, but are not limited to, any of the standard pharmaceutical carriers such as a phosphate buffered saline solution, water, emulsions such as oil/water emulsions, and various types of wetting agents. Compositions comprising such carriers are formulated by well known conventional methods (see, for example, Remington's Pharmaceutical Sciences, Chapter 43, 14th Ed., Mack Publishing Co., Easton, Pa.)

The term "conjugate" means a compound formed as a composite between two or more molecules. More specifically, in the present invention, the quinazoline derivative is bonded, for example, covalently bonded, to cell-specific targeting moieties forming a conjugate compound for efficient and specific delivery of the agent to a cell of interest.

The phrase "targeting moiety" means a molecule which serves to deliver the compound of the invention to a specific site for the desired activity. Targeting moieties include, for example, molecules that specifically bind molecules on a specific cell surface. Such targeting moieties useful in the invention include anti-cell surface antigen antibodies. Cytokines, including interleukins and factors such as granulocyte/macrophage stimulating factor (GMCSF) are also specific targeting moieties, known to bind to specific cells expressing high levels of their receptors.

Particularly useful targeting moieties for targeting the compound of the invention to mast cells include antibodies and receptor ligands to mast cell antigens such as CD48, CD13, or to the SCF, GMCSF, or IL-3 receptors of mast cells. Many such antibodies and ligands are known, and are commercially available, for example TXU145 (anti-CD48) and WM15 (anti-CD13) available from PharMignen (Torrey Pines, Calif.). Useful antibodies also include MY7 and MCS2 (anti-CD13), disclosed in Myers et al., 1988, *Transparitatiox*, 46:240–244. Recombinant IL-3, GMSCF, and SCF are also commercially available.

The term "prodrug moiety" is a substitution group which facilitates use of a compound of the invention, for example by facilitating entry of the drug into cells or administration of the compound. The prodrug moiety may be cleaved from the compound, for example by cleavage enzymes in vivo. Examples of prodrug moieties include phosphate groups, peptide linkers, and sugars, which moieties can be hydrolized in vivo.

The phrase "potentiating" is meant to define inducement and/or enhancement of activity over a non-stimulated control. The term "microbiocidal" means an activity that results in the death of microorganisms such as bacteria and other infectious microbial organisms.

Another specific group of compounds are compounds of formula I wherein $R_3$ and $R_4$ are each independently hydrogen, $(C_1-C_4)$alkyl, halo, or $(C_1-C_4)$alkanoyl; or $R_3$ and $R_4$ together are methylenedioxy; or a pharmaceutically acceptable salt thereof.

COMPOUNDS OF THE INVENTION

The compounds of the invention are quinazoline derivatives having a hydroxy substitution on the phenyl ring $(R_1)$ and one or more halo substitution $(R_2)$. The structure is represented by the following compound:

The compounds of the invention include at least one hydroxy group substituted on the phenyl ring ($R_1$ is OH), preferably at the 3', 4', or 5' position. In addition, the compounds of the invention include one or more halogen substitution, e.g., one or more $R_2$, preferably from one to four $R_2$ substitutions are made on the phenyl ring ($R_2$ is halo, and n is 1–4). Preferably at least one halogen is substituted at the 3', 4', or 5' position. Most preferably, a single halogen is substituted.

The halo group can be any of Br, Cl, F, or I, but is preferably Br. The preferred positions for the substitutions is 3'-Br, 4'-OH.

The $R_1-R_2$ substituted phenyl 1 ring appears to be the portion of the compound responsible for mast-cell potentiating activity. The opposite end of the molecule, e.g., the $R_3-R_4$ substituted phenyl ring may be considerably modified, e.g., by substitution at $R_3$ and $R_4$, for example by providing a prodrug moiety or other substitution facilitating use of the compound. $R_3$ and $R_4$ can independently be $(C_1-C_4)$alkyl, $(C_1-C_4)$alkoxy, halo, or $(C_1-C_4)$alkanoyl; or $R_3$ or $R_4$ together are methylenedioxy, $R_3$ or $R_4$ can be a prodrug derivative, that is, a functional group that facilitates use of the drug in the body, for example, by facilitating entry into cells. The prodrug derivative may be cleaved or not in the active compound. Preferably, $R_3$ and $R_4$ are each $CH_3O_1$.

A particularly preferred compound of the invention is 4-(3'bromo-4'-hydroxyphenyl)-amino-6,7-dimethoxyquinazoline.

As discussed in the Examples below, data suggests the single halogen, (e.g., 3'-bromo-) and single hydroxy (e.g., 4-OH) substituted phenyl ring is required for the observed potentiation of mast cell antimicrobial activity, as structurally similar compounds lacking this bromo substituent were not active. Introduction of a second bromo group did not increase activity.

The useful compounds of the invention, including 4-(3'-bromo-4'-hydroxyphenyl)-amino-6,7-dimethoxyquinazoline, can be synthesized as described in the Examples below.

Conjugate Formation

To form the conjugates of the invention, targeting moieties are covalently bonded to sites on the quinazoline compound. The targeting moiety, which is often a polypeptide molecule, is bound to compounds of the invention at reactive sites, including $NH_2$, SH, CHO, COOH, and the like. Specific linking agents are used to join the compounds. Preferred linking agents are chosen according to the reactive site to which the targeting moiety is to be attached.

Methods for selecting an appropriate linking agent and reactive site for attachment of the targeting moiety to the compound of the invention are known, and are described, for example, in Hermanson, et al., *Bioconjugate Techniques*, Academic Press, 1996; Hermanson, et al., *Immobilized Affinity Ligand Techniques*, Academic Press, 1992; and *Pierce Catalog and Handbook*, 1996, pp. T155–T201.

Treatment Methods

The compounds of the invention are useful to potentiate and enhance bacterial clearance and the antimicrobial activity of mast cells. Such enhanced mast cell activity is clinically useful, for example, in the treatment of infections, and in particular, in the treatment of infections that are secondary to chemotherapy, bone marrow transplantation, and radiotherapy, for an example as a result of neutropeuia. Administration of the compounds of the invention results in enhanced bacterial clearance. The treatment method of the invention is particularly useful in patients suffering neutrophil disorders and are therefore at high risk for infection. Such neutropeuia may be due to inborn errors, disease conditions (uremia, chronic granulomatosis disease (CTG)), or due to chemotherapy, radiation therapy, or bone marrow transplantation. In these patients, reduction of numbers or function of neutrophils is compensated by enhanced MAST cell antimicrobial activity induced by the compounds of the invention.

Administration Methods

The compounds and conjugates of the present invention can be formulated as pharmaceutical compositions and administered to a mammalian host, including a human patient in a variety of forms adapted to the chosen route of administration and suitable for administration of the small molecule or its conjugate. Preferred administration routes include orally, parenterally, as well as intravenous, intramuscular or subcutaneous routes.

It is most preferred that the compound or conjugate of the present invention be administered parenterally, i.e., intravenously or intraperitoneally, by infusion or injection. In one embodiment of the invention, the compounds may be administered by systemic delivery by intravenous injection. The compounds of the invention, including the conjugates, are of a size and composition expected to have ready access to mast cells and macrophages.

Solutions or suspensions of the compounds and conjugates can be prepared in water, isotonic saline (PBS) and optionally mixed with a nontoxic surfactant. Dispersions may also be prepared in glycerol, liquid polyethylene, glycols, DNA, vegetable oils, triacetin and mixtures thereof. Under ordinary conditions of storage and use, these preparations may contain a preservative to prevent the growth of microorganisms.

The pharmaceutical dosage form suitable for injection or infusion use can include sterile, aqueous solutions or dispersions or sterile powders comprising an active ingredient which are adapted for the extemporaneous preparation of sterile injectable or infusible solutions or dispersions. In all cases, the ultimate dosage form should be sterile, fluid and stable under the conditions of manufacture and storage. The liquid carrier or vehicle can be a solvent or liquid dispersion medium comprising, for example, water, ethanol, a polyol such as glycerol, propylene glycol, or liquid polyethylene glycols and the like, vegetable oils, nontoxic glyceryl esters, and suitable mixtures thereof. The proper fluidity can be maintained, for example, by the formation of liposomes, by the maintenance of the required particle size, in the case of dispersion, or by the use of nontoxic surfactants. The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers, or sodium chloride. Prolonged absorption of the injectable compositions can be brought about by the inclusion in the composition of agents delaying absorption—for example, aluminum monosterate hydrogels and gelatin.

Sterile injectable solutions are prepared by incorporating the conjugates in the required amount in the appropriate solvent with various other ingredients as enumerated above and, as required, followed by filter sterilization. In the case of sterile powders for the preparation of sterile injectable solutions, the preferred methods of preparation are vacuum drying and freeze-drying techniques, which yield a powder of the active ingredient plus any additional desired ingredient present in the previously sterile-filtered solutions.

Useful Dose

When used in vivo to potentiate the antimicrobial activity of mast cells, the administered dose is that effective to have the desired effect, e.g., sufficient to induce and enhance antimicrobial activity of mast cells and to enhance bacterial clearance. Desired effects of the compound via induced mast cell antimicrobial activity include rapid conversion of positive blood cultures in bacteriamic patients to negative blood cultures; reduced fever; reduced incidence of septic shock; and a reduction in the duration of systemic antibiotic therapy required for clinical effect.

Appropriate amounts can be determined by those skilled in the art, extrapolating using known methods and relationships, from the in vitro and in vivo data provided in the Examples. Based on the mouse pharmacology data contained in this application, effective exposure levels are expected to be achieved.

In general, the dose of the hydroxy-halo-quinazolines, e.g., 4-(3'bromo-4'-hydroxyphenyl)-amino-6,7-dimethoxyquinazoline, effective to achieve potentiation of mast cell antimicrobial activity and/or enhanced bacterial clearance in a patient, is that which administers micromolar amounts of the compound to the cells, preferably about 10 micromolar or greater. The required dose is lessened by conjugation of the compound to a targeting moiety, for example, to preferably about 10 nanomolar or greater concentrations.

The effective dose to be administered will vary with conditions specific to each patient. In general, factors such as the disease burden, host age, metabolism, sickness, prior exposure to drugs, and the like contribute to the expected effectiveness of a drug. One skilled in the art will use standard procedures and patient analysis to calculate the appropriate dose, extrapolating from the data provided in the Examples.

In general, a dose which delivers about 1–100, preferably 5–10 mg/kg body weight is expected to be effective, although more or less may be useful.

In addition, the compositions of the invention may be administered in combination with other anti-bacterial therapies.

The invention may be better understood by reference to the following Examples.

EXAMPLES

Example 1

Effect of dimethoxyquinazolines on mast cell bactericidal activity

Mast cells were cultured from the bone marrow cells of 6–8 week old Balb/c mice as described previously (Malaviya, R., et al., 1993, *J. Biol Chem.*, 286(7):4939–44 and Malaviya, R., et al., 1995, *Methods Enzymol.*, 253:37–43). In brief, bone marrow cells were grown in 225 $cm^2$ tissue culture flasks in enriched RPMI-1640 medium containing 25% WEHI-3 condition media. Mast cells harvested from these cultures were ≧98% pure as determined by toluidine blue staining. A well characterized K12 strain *E. coli* ORN103, bearing the recombinant plasmid pSH2 encoding type 1 fimbriae (Malaviya, R., et al., 1995, *Methods Enzymol.*, 253:27–43 and Tewari., R., et al., 1993, *J. Biol. Chem.*, 268 (4):3009–15) was also used. *E. coli* ORN103(pSH2) and mast cells were previously used as an in vitro model system to demonstrate that mast cells possess bactericidal activity against gram negative bacteria (Malaviya, R., et al., 1994, *J. Immunol.*, 152 (4):1907–14).

To study the effect of dimethoxyquinazolines in the mast cell *E. coli* model, WHI-P154, WHI-P131, WHI-P132, WHI-P97, and WHI-P112 were prepared by condensation of 4-chloro-6,7-dimethoxyquinazoline and substituted anilines as recently described in detail (Goodman, P, et al., 1998, *J. Biol. Chem.*, 273 (28):17742–8).

The structures of these compounds are shown below:

4-(3',5'-Dibromo-4'-hydroxylphenyl)-amino-6,7-dimethoxyquinazoline [WHI-P97]

yield 72.80%; m.p.>300.0° C. UV(MeOH)$\lambda_{max}$: 208.0, 210.0, 245.0, 320.0 nm; IR(KBr)$v_{max}$: 3504(br), 3419, 2868, 1627, 1512, 1425, 1250, 1155 $cm^{-1}$; $^1$H NMR(DMSO-$d_6$): δ 9.71(s, 1H, —NH), 9.39(s, 1H, —OH), 8.48(s, 1H, 2-H); 8.07(s, 2H, 2', 6'-H), 7.76(s, 1H, 5-H), 7.17(s, 1H, 8-H), 3.94(s, 3H, —OCH$_3$), 3.91(s, 3H, —OCH$_3$). GC/MS m/z 456($M^+$ +1, 54.40), 455($M^+$, 100.00), 454($M^+$-1, 78.01), 439($M^+$ —OH, 7.96), 376($M^+$ +1 —Br, 9.76), 375($M^+$ —Br, 10.91), 360(5.23). Anal. ($C_{16}H_{13}Br_2N_3O_3$) C, H, N.

4-(4'-Hydroxyphenyl)-amino-6,7-dimethoxyquinazoline [WHI-P131]

yield 84.29%; m.p. 245.0–248.0.° C. UV(MeOH)$\lambda_{max}$: 203.0, 222.0, 251.0, 320.0 nm; IR(KBr)$v_{max}$: 3428, 2836, 1635, 1516, 1443, 1234 $cm^{-1}$; $^1$H NMR(DMSO-$d_6$): δ 11.21(s, 1H, —NH), 9.70(s, 1H, —OH), 8.74(s, 1H, 2-H), 8.22(s, 1H, 5-H), 7.40(d, 2H, J=8.9 Hz, 2', 6'-H), 7.29(s, 1H, 8-H), 6.85(d, 2H, J=8.9 Hz, 3', 5'-H), 3.98(s, 3H, —OCH$_3$), 3.97(s, 3H, —OCH$_3$). GC/MS m/z 298 ($M^+$ +1, 100.00), 297($M^+$, 26.56), 296($M^-$-1, 12.46). Anal. ($C_{16}H_{15}N_3O_3$HCl) C, H, N.

4-(2'-Hydroxyphenyl)-amino-6,7-dimethoxyquinazoline [WHI-P132]

yield 82.49%; m.p. 255.0–258.0° C. $^1$H NMR(DMSO-$d_6$): δ 9.78(s, 1H, —NH), 9.29(s, 1H, —OH), 8.33(s, 1H, 2-H), 7.85(s, 1H, 5-H), 7.41–6.83(m, 4H, 3', 4', 5', 6'-H), 7.16(s, 1H, 8-H), 3.93(s, 3H, —OCH$_3$), 3.92(s, 3H, —OCH$_3$). UV(mEoh)$\lambda_{max}$(ε): 203.0, 224.0, 245.0, 335.0 nm. IR(KBr)$v_{max}$: 3500(br), 3425, 2833, 1625, 1512, 1456, 1251, 1068 $cm^{-1}$. GC/MS m/z 298($M^+$ +1, 8.91), 297($M^+$, 56.64), 281($M^+$+1 —OH, 23.47), 280($M^+$-OH, 100.00). Anal. ($C_{16}H_{15}N_3O_3$HCl) C, H, N.

-continued 4-(3'-Bromo-4'-hydroxyphenyl)-amino-6,7-dimethoxyquinazoline [WHI-P154]

yield 89.90%; m.p. 233.0–233.5° C. UV(MeOH)$\lambda_{max}$: 203.0, 222.0, 250.0, 335.0 nm; IR(KBr)$\nu_{max}$: 3431 br, 2841, 1624, 1498, 1423, 1244 cm$^{-1}$; $^1$H NMR(DMSO-d$_6$): δ 10.08(s, 1H, —NH), 9.38(s, 1H, —OH), 8.40(s, 1H, 2-H), 7.89(d, 1H, $J_{2',5'}$=2.7Hz, 2'-H), 7.75(s, 1H, 5-H), 7.55(dd, 1H, $J_{5',6'}$=9.0 Hz, $J_{2',6'}$=2.7 Hz, 6'-H), 7.14(s, 1H, 8-H), 6.97(d, 1H, $J_{5',6'}$=9.0 Hz, 5'-H), 3.92(s, 3H, —OCH$_3$), 3.90(s, 3H, —OCH$_3$). GC/MS m/z 378(M$^+$ +2, 90.68), 377(M$^+$ +1, 37.49), 376(M$^+$, 100.00), 360(M$^+$, 3.63), 298(18.86), 282 (6.65). Anal. (C$_{16}$H$_{14}$N$_3$O$_3$HCl) C, H, N.

The effect of dimethoxyquinazolines on the viability of bone marrow cultured mast cells (BMMC) and type 1 fimbriated E. coli ORN103(pSH2) was first tested. During an incubation time of 2 hours, these compounds did not affect viability of mast cells as assessed by trypan blue dye exclusion test, or E. coli ORN103(pSH2) as assessed by disc MIC test.

To study the effects of the quinazoline derivatives on mast cell bactericidal activity, mast cell monolayers were incubated with 100 μM WHI-P154, WHI-P131, WHI-P132, WHI-P97, or WHI-P112 for 1 hour prior to challenge with 3×10$^7$ E. coli for 15 minutes. Monolayers were washed several times to remove unbound bacteria. Fresh media was added to each well and the plate was further incubated for 0 or 30 minutes. Monolayers were treated with an equal volume of 0.2% Triton X-100 to disrupt the cell membrane. The viable bacteria were quantitated by determining the number of CFU from serial dilutions of the cell lysate plated on MacConkey agar as has been described previously (Malaviya, R., et al., 1994, J. Immunol., 152 (4):1907–14 and Malaviya, R., et al., 1995, Methods Enzymol, 253:27–43).

Figure 1:
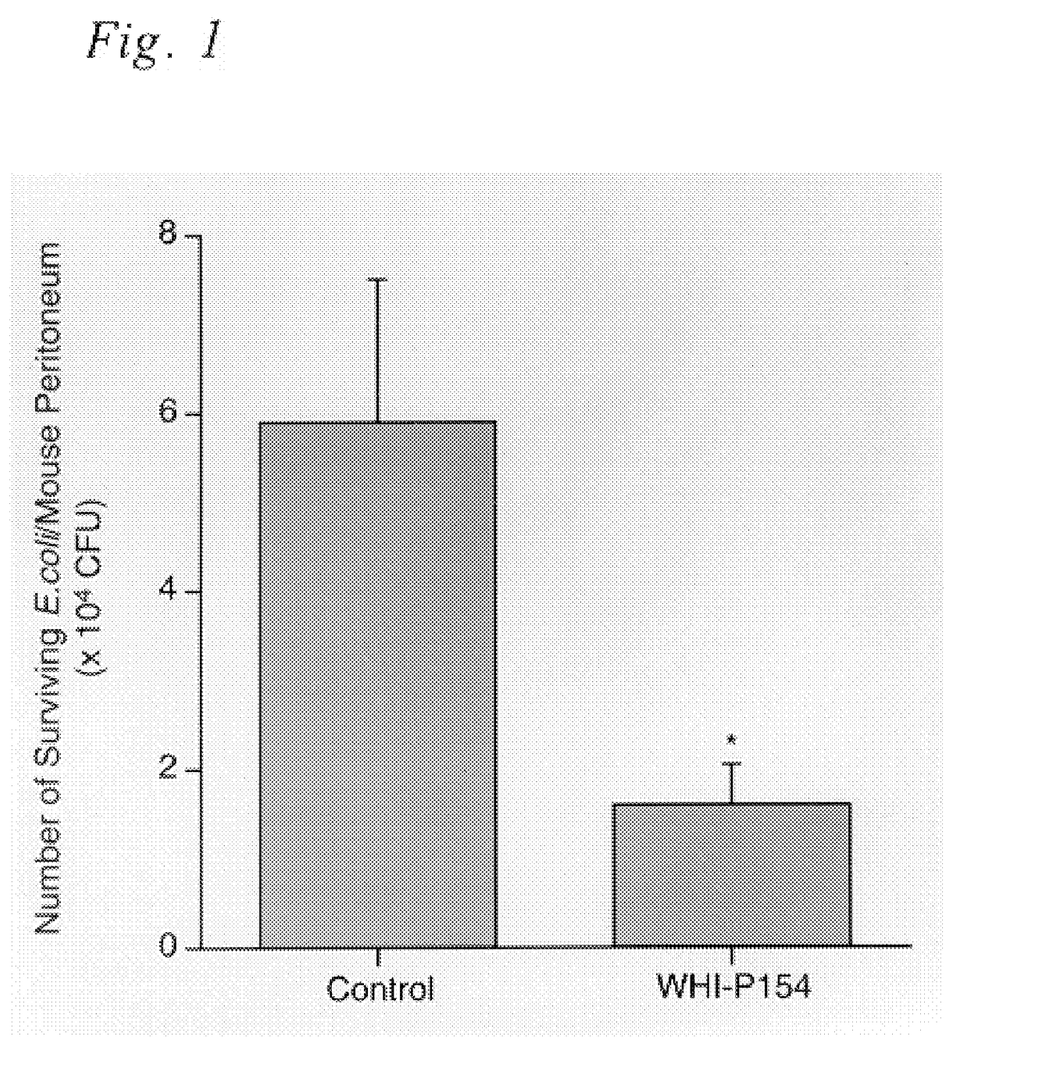
Figure 2:
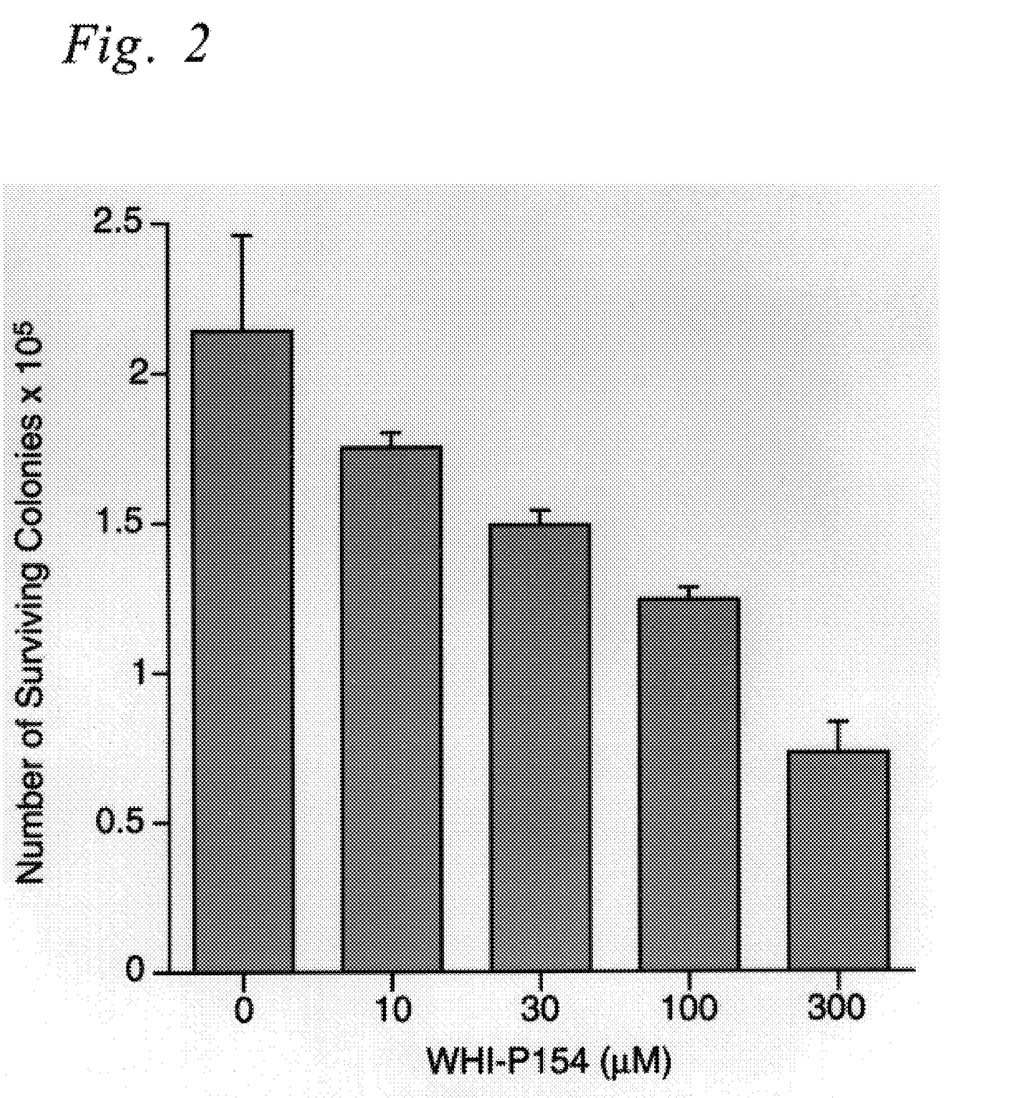
FIG. 2 is a graph demonstrating augmentation of mast cell bactericidal activity by WHI-P154. Mast cell monolayers were treated with the indicated concentrations of WHI-P154 or vehicle prior to bacterial challenge. The number of viable bacteria associated with mast cell monolayers was determined. The results are expressed as number of CFU/mast cell monolayer.

FIG. 1 shows that mast cells kill approximately 50% of adherent E. coli within 30 minutes. Further, addition of quinazoline derivative 4-(3'bromo-4'-hydroxylphenyl)-amino-6,7-dimethoxyquinazoline (WHI-P154), but not WHI-P131, WHI-P132, or WHI-P112, potentiated mast cell bactericidal activity and reduced bacterial viability to about 25%. The structurally similar WHI-P97 also produced an effect, albeit less pronounced on mast cell bactericidal activity (FIG. 1). Further, the effect of WHI-P154 on mast cell bactericidal activity was dose dependent (FIG. 2). The bacterial viability dropped to approximately 20% after incubation with 300 μM WHI-P154.

Since the ability of mast cells to kill bacteria depends on their phagocytic activity, which is directly related to the number of bacteria that adhere to mast cells (Malaviya, R., et al., 1994, J. Immunol., 152 (4):1907–14 and Malavia, R., et al., 1996, J. Immunol., 152 (4):1490–6) we sought to investigate the effect of WHI-P154 on the ability of mast cells to bind type 1 fimbriated E. coli ORN103(pSH2). To achieve this, mast cell monolayers were incubated with vehicle or the indicated concentrations of WHI-P154 for 1 hour prior to exposure to 1×10$^7$FITC labeled (for confocol microscopy) or unlabeled (for light microscopy) type 1 fimbriated E. coli ORN103(pSH2) for 30 minutes. Unbound bacteria were removed by repeated washing. Cells bound with FITC labeled E. coli were visualized under laser confocal microscope and cells bound with unlabeled E. coli were counted under light microscope after fixing and staining with crystal violet.

Figure 3:
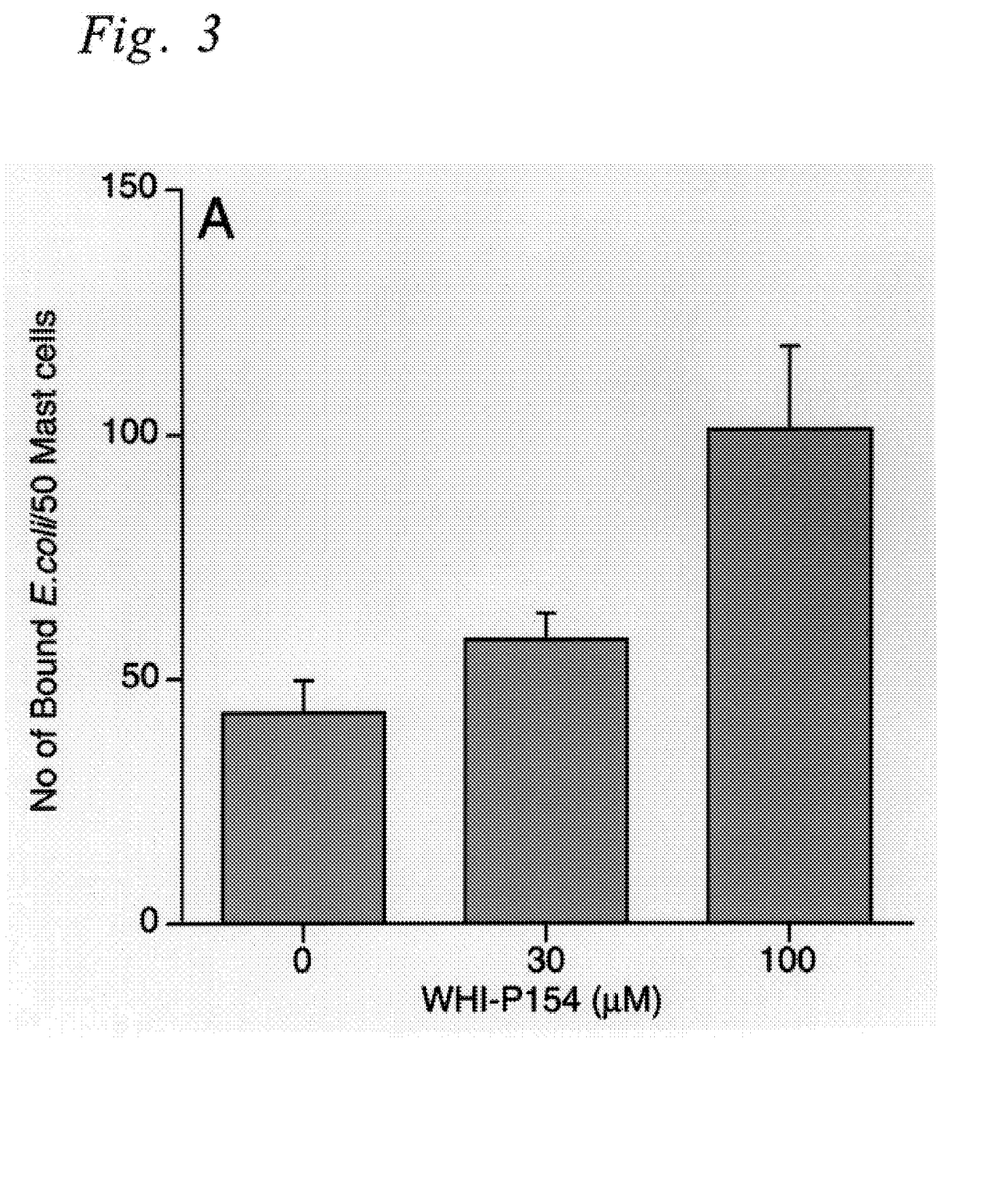
FIG. 3 is a graph demonstrating potentiation of *E. coli* adherence to mast cells by WHI-P154. Mast cells were incubated with *E. coli* and stained with crystal violet. The number of adherent bacteria were counted under light microscopy. The data points represent the mean ± SEM values from 3 independent experiments.
Figure 4A:
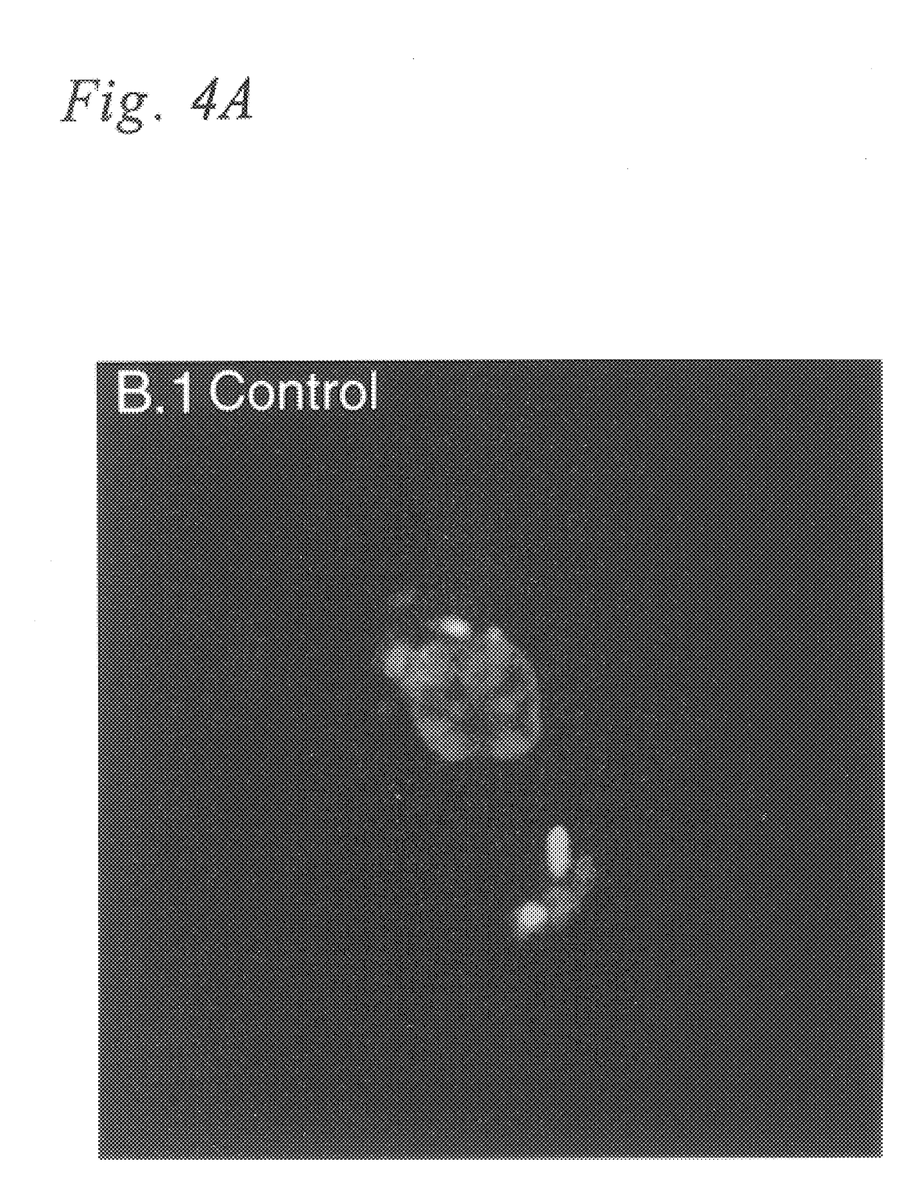
FIGS. 4A and 4B are confocal images of mast cells incubated with FITC labeled *E. coli* and showing bacterial binding to control (4A) and WHI-P154 treated (4B) mast cells.
Figure 4B:
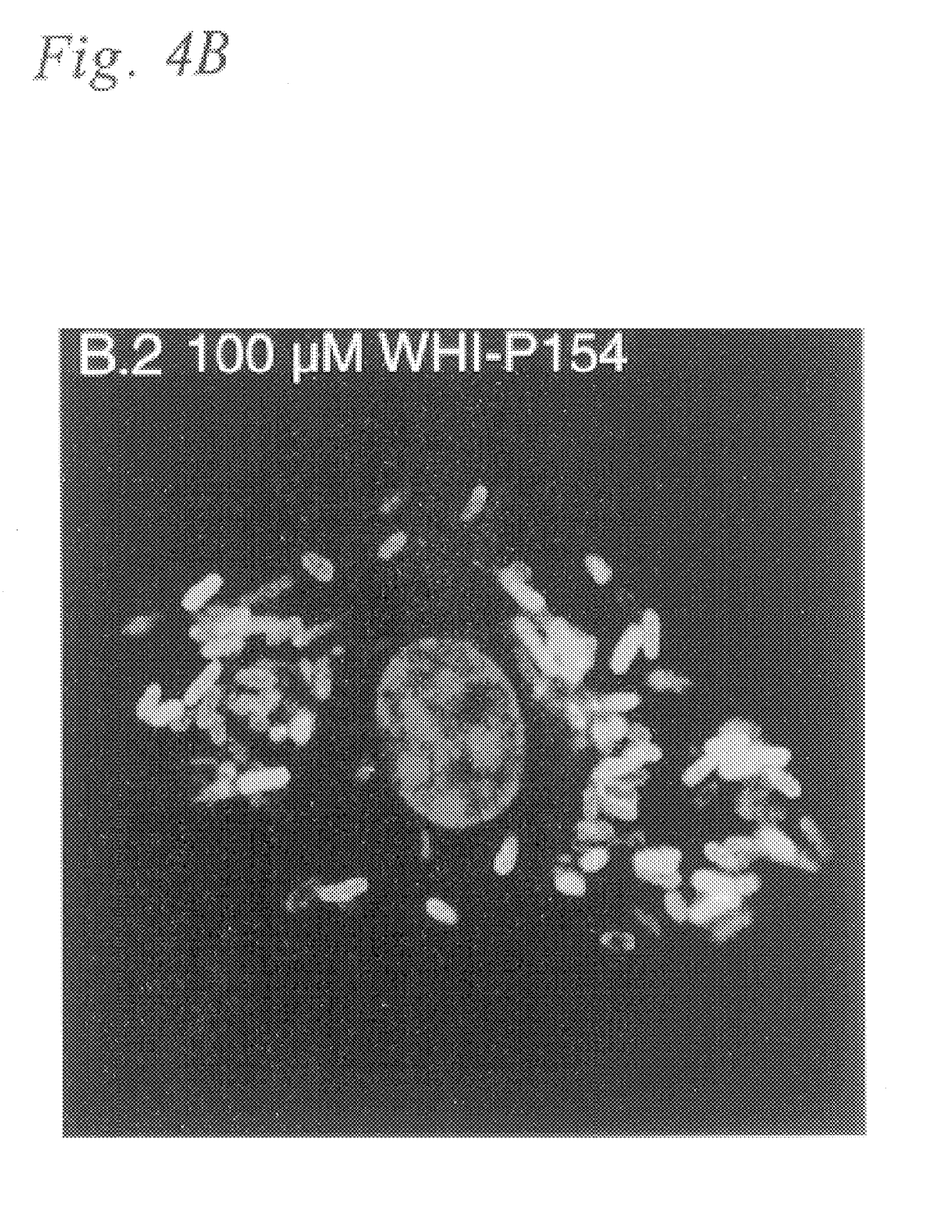

As shown in FIG. 3, WHI-P154 increased E. coli ORN103(pSH2) binding to mast cells in a dose-dependent fashion. Laser confocol microscopy (FIGS. 4A and 4B) also confirmed that WHI-P154 increased bacterial binding to mast cells.

Figure 5A:
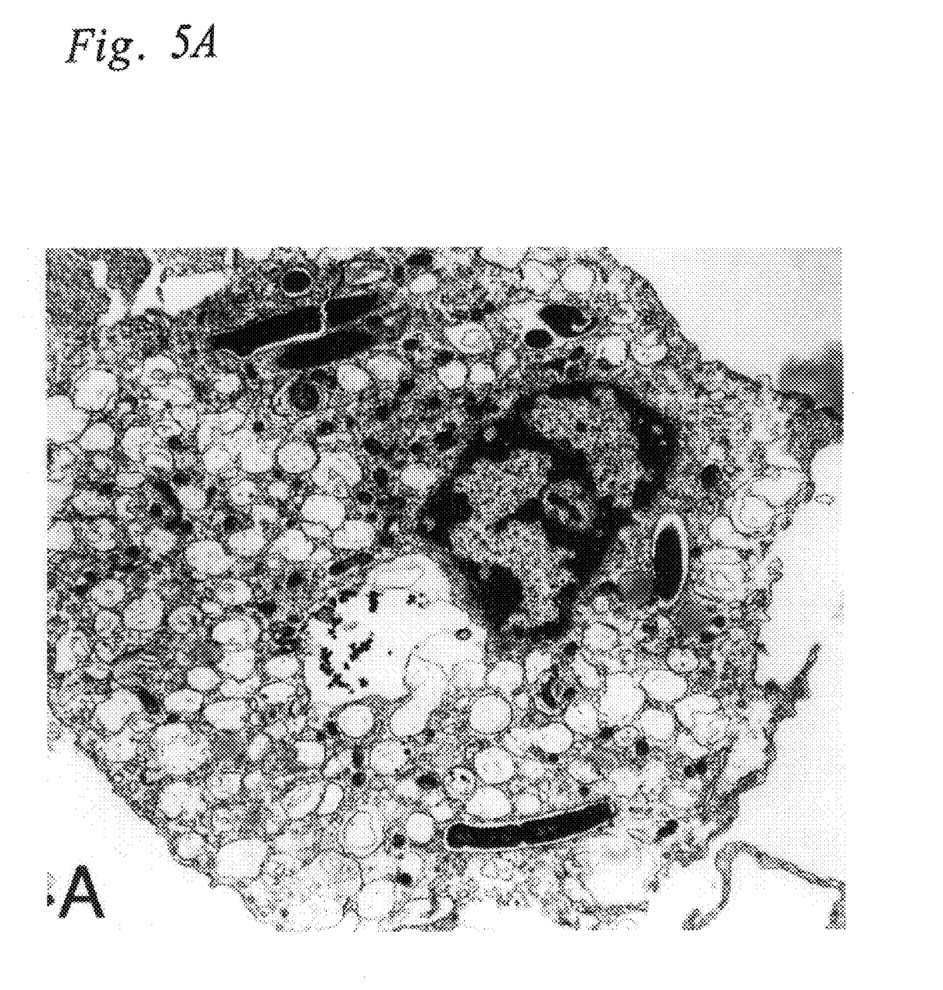
FIGS. 5A and 5B are transmission electron micrographs demonstrating potentiation of mast cell phagocytic activity by WHI-P154. Micrographs show mast cell cross sections treated with vehicle (5A) or WHI-P154 (5B) prior to E. coli challenge.
Figure 5B:
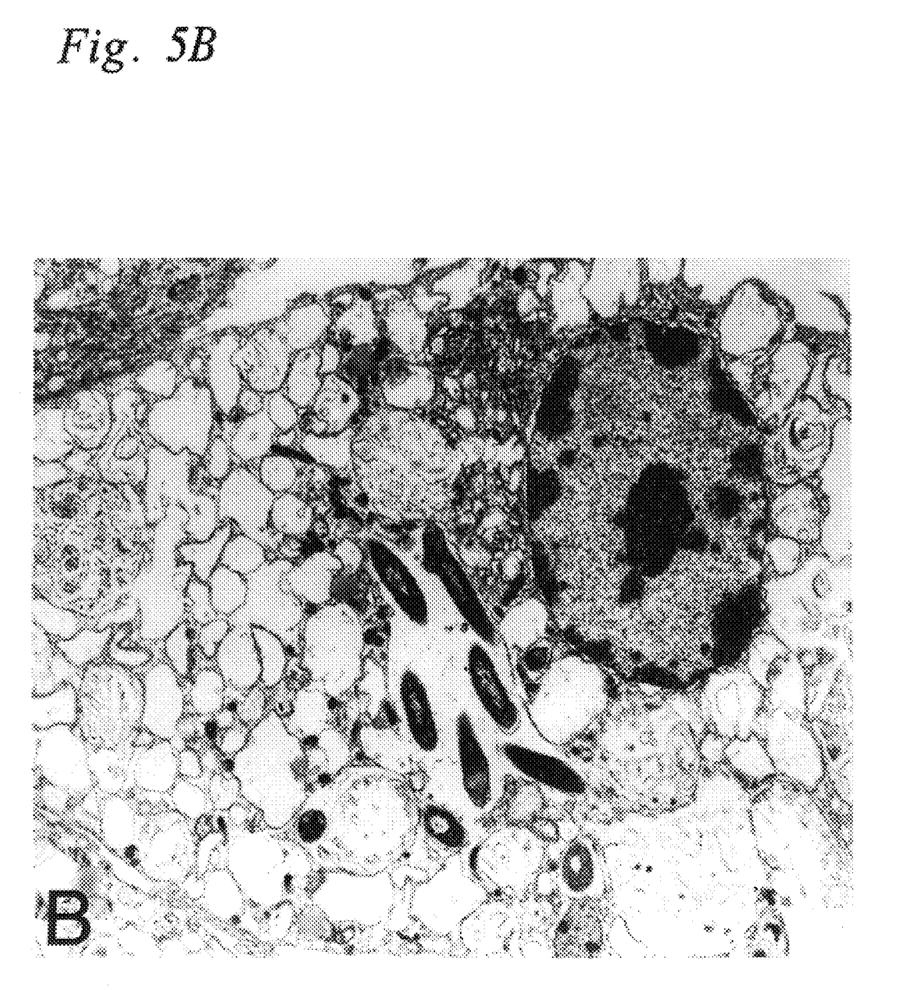

To show that increased bacterial binding results in enhanced phagocytosis of bacteria, mast cells were incubated with vehicle or 100 μM WHI-P154 for 1 hour and then exposed to E. coli ORN103(pSH2) for 30 minutes. Unbound bacteria were removed by repeated washing and the mast cells were fixed in 2% glutaraldehyde and embedded in resin for transmission microscopy. Electron microscopic examination of thin sections of these cells revealed that mast cells pretreated with WHI-P154 engulfed more bacteria than untreated mast cells (FIGS. 5A and 5B). Further, untreated mast cells contained bacteria in tight vacuoles (FIG. 5A) whereas WHI-P154 treated mast cells contained bacteria in large spacious phagocytic vacuoles (FIG. 5B). Thus, increased bacterial binding results in more efficient bacterial uptake and killing by mast cells after pretreatment with WHI-P154.

Example 2

Administration of WHI-P154 enhances bacterial clearance

Figure 6:
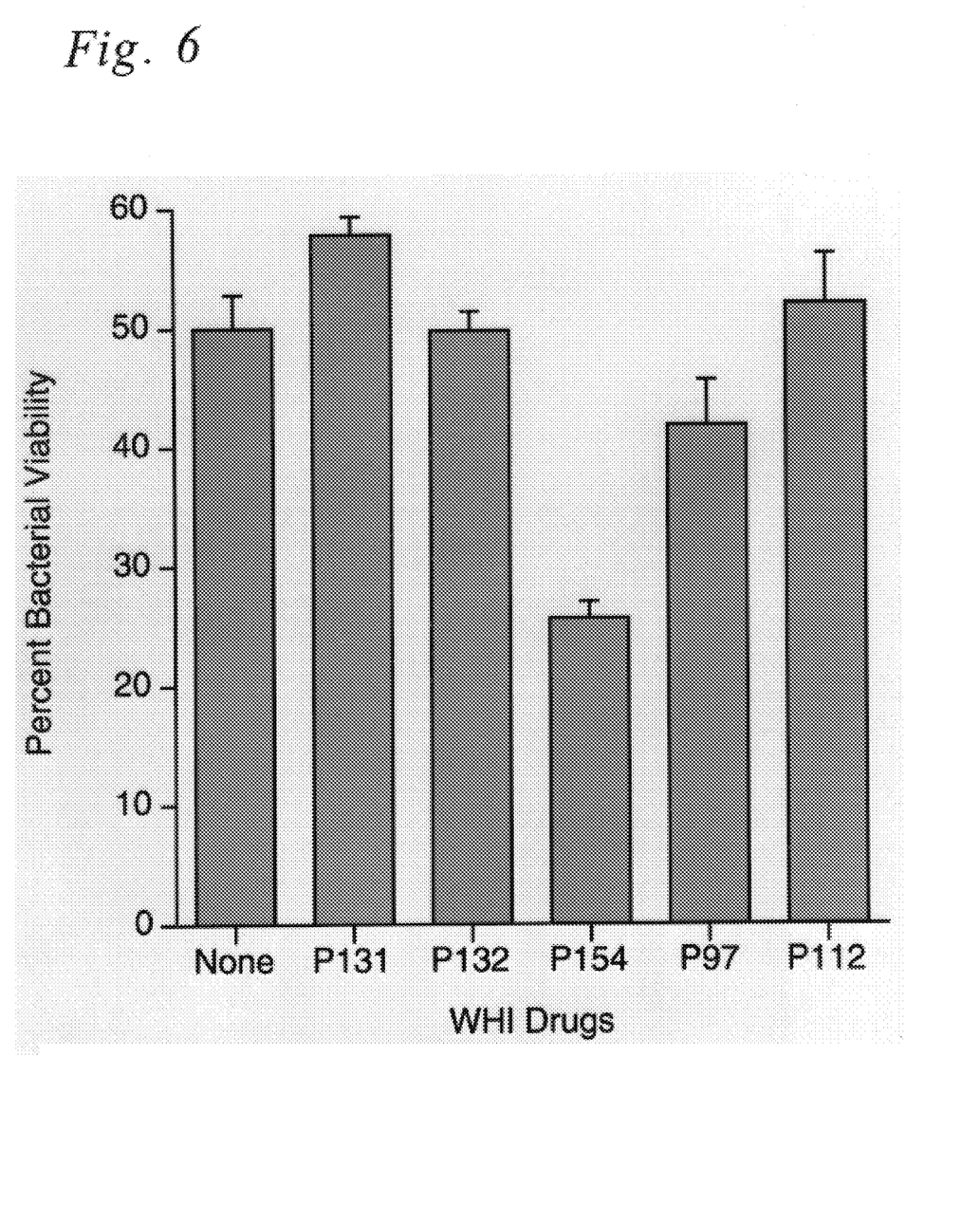
FIG. 6 is a graph showing increased bacterial clearance in the peritoneum of WHI-P154 treated mice. The number of viable E. coli was determined in the peritoneum of Balb/c mice pretreated with vehicle or WHI-P154. Results were expressed as number of colony forming units (CFU)/peritoneum. The data points represent the mean ±SEM. n=5 mice; *p<0.05.

To further demonstrate the physiological relevance of the in vitro findings, the effect of WHI-P154 on bacterial clearance was tested in a mouse model of bacterial peritonitis. Balb/c mice were injected intraperitoneally with 10 mg/kg WHI-P154 or an equal volume of vehicle (10% DMSO). After 15 minutes, mice were challenged with 4×10$^7$ E. coli ORN103(pSH2) intraperitoneally (Malaviya, R., et al., 1996, Nature, 381 (6577):77–80 and Malaviya, R., et al., 1994, J. Clin Invest., 93 (4):1645–53). Bacterial viability was determined in peritoneal lavages of the mice after 2 hours of bacterial challenge (Malaviya, R., et al., 1996, Nature, 381 (6577):77–80). When the number of surviving bacteria in the mouse peritoneum were compared, mice pretreated with WHI-P154 demonstrated significantly reduced surviving bacteria in their peritoneum than vehicle treated controls (1.6×10$^4$Vs 5.9×10$^4$, p<0.05) (FIG. 6).

WHI-P154 has no bactericidal activity against E. coli at the tested concentrations, therefore it is concluded that WHI-P154 exerts its effect on mast cells rather than bacteria. The observation that WHI-P154 potentiates mast cell microbicidal activity comes from the finding that WHI-P154 treated mast cells have fewer surviving bacteria than control mast cells as shown by bacteria viability assays. Thus, WHI-P154 potentiated mast cell bactericidal activity by augmenting phagocytic activity of mast cells. The experimental data show that WHI-P154 treated mast cells bind more bacteria and possess several bacteria per phagocytic vacuole as compared to control mast cells which contain one bacteria per vacuole. The mechanism by which WHI-P154 augments increased bacterial binding to mast cells is not known.

The in vivo data provided direct evidence that WHI-P154 potentiates bacterial killing and clearance. Further, it is reasonable to believe that WHI-P154 is modulating bactericidal activity of macrophages.

In conclusion, these data are consistent with the observation that WHI-P154 potentiates the microbioidal activity of mast cells. While these results could be attributed solely to mast cell potentiation by WHI-P154, it is possible that additional, non-mast cell elements of the immune system are also potentiated in vivo, leading to a more effective overall immune response. WHI-P154 may contribute to more efficient bacterial clearance particularly in patients with the defects of phagocytic components of the immune system, such as neutropenia.

This application recites numerous publications which are hereby incorporated by reference for all purposes, as if fully set forth herein. The invention has been described with reference to various specific and preferred embodiments and techniques. However, it should be understood that many variations and modifications may be made while remaining within the spirit and scope of the invention.

We claim:

1. A method for potentiating microbicidal activity of mast cells in a patient comprising: administering to the patient a compound of the formula:

(I)

where $R_1$ is OH; $R_2$ is halo, and n is 1–4; $R_3$ and $R_4$ are independently selected from halo, $(C_1-C_4)$alkyl, $(C_1-C_4)$ alkoxy, $(C_1-C_4)$alkanoyl, or a prodrug moiety, or $R_3$ and $R_4$ together are methylene dioxy.

2. The method of claim 1, wherein n is 1 or 2.

3. The method of claim 1, wherein $R_1$ is positioned at the 3', 4', or 5' position of the phenyl ring.

4. The method of claim 1, wherein one or more halogen is positioned at the 3', 4', or 5' position of the phenyl ring.

5. The method of claim 1, wherein $R_1$ is positioned at the 4' position and $R_2$ is positioned at the 3' position of the phenyl ring.

6. The method of claim 1, comprising administering a compound of the formula:

7. The method of claim 1, comprising administering a compound of the formula:

8. A method for enhancing antibacterial activity and bacterial clearance in a patient, the method comprising administering to the patient a compound of the formula (I)

where $R_1$ is OH; $R_2$ is halo, and n is 1–4; $R_3$ and $R_4$ are independently selected from halo, $(C_1-C_4)$alkyl, $(C_1-C_4)$ alkoxy, $(C_1-C_4)$alkanoyl, or a prodrug moiety, or $R_3$ and $R_4$ together are methylene dioxy.

9. A method for treating microbial infection in a patient, comprising administering to the patient's mast cells a compound of the formula (I)

where $R_1$ is OH; $R_2$ is halo, and n is 1–4; $R_3$ and $R_4$ are independently selected from halo, $(C_1-C_4)$alkyl, $(C_1-C_4)$ alkoxy, $(C_1-C_4)$alkanoyl, or a prodrug moiety, or $R_3$ and $R_4$ together are methylene dioxy.

10. The method of claim 1, wherein said patient is neutropenic.

11. The method of claim 1, wherein said compound is conjugated to an antibody or receptor ligand which specifically binds CD48, CD13, SCF receptor, GMCSF receptor, or IL-3 receptor.

12. The method of claim 1, wherein said halo is Br.

13. The method of claim 1, wherein said halo is F.

14. The method of claim 1, wherein said halo is Cl.

15. The method of claim 1, wherein said halo is I.

* * * * *